United States Patent [19]

Sandler et al.

[11] Patent Number: 5,068,427
[45] Date of Patent: Nov. 26, 1991

[54] PROCESS FOR THE PREPARATION OF ALKANE- AND ARENESULFONAMIDES

[75] Inventors: Stanley R. Sandler, Springfield; Steven G. Schon, Strafford; David M. Gardner, King of Prussia, all of Pa.

[73] Assignee: Atochem North America, Inc., Philadelphia, Pa.

[21] Appl. No.: 438,389

[22] Filed: Nov. 16, 1989

[51] Int. Cl.$^5$ .......................................... C07C 303/38
[52] U.S. Cl. ...................... 564/84; 564/90; 564/92; 564/95; 564/98
[58] Field of Search ................ 564/92, 90, 84, 98

[56] References Cited

U.S. PATENT DOCUMENTS

| | | | |
|---|---|---|---|
| 2,334,186 | 11/1943 | Fox | 564/98 |
| 2,554,816 | 5/1950 | Clapp et al. | 546/119 |
| 3,034,955 | 5/1962 | Frick | 564/92 |
| 3,300,529 | 6/1967 | Berkelhammer et al. | 564/95 |
| 3,574,740 | 2/1971 | Martin | 564/98 |
| 3,624,150 | 11/1971 | Albrecht Renner et al. | 564/92 |
| 3,755,439 | 8/1973 | Kennedy | 564/98 |
| 3,781,441 | 11/1973 | Collins | 514/603 |

FOREIGN PATENT DOCUMENTS

| | | |
|---|---|---|
| 235626 | 4/1986 | Czechoslovakia . |
| 0276182 | 3/1988 | European Pat. Off. . |
| 2003059 | 11/1969 | France ................ 564/92 |
| 0940128 | 10/1963 | United Kingdom ......... 564/90 |

OTHER PUBLICATIONS

Chem. Abstract 56:7116f (1968).
Dutt. J. Chem. Soc., vol. 125, pp. 1463-1465 (1924).
Chem. Abstract 43:120f (1948).
Sacco et al., J. Am. Chem. Soc., vol. 76, pp. 303-305 (1985).
Field et al., J. Am. Chem. Soc., vol. 75, pp. 934-937 (1953).
Field et al., J. Am. Chem. Soc., vol. 77, pp. 170-171 (1955).
Chem. Abstract 53:1140i (1959).

*Primary Examiner*—Glennon H. Hollrah
*Assistant Examiner*—Susan P. Treanor
*Attorney, Agent, or Firm*—Seidel, Gonda, Lavorgna & Monaco

[57] ABSTRACT

A process for the preparation of alkane- and arenesulfonamides in high purity and yield is provided. Ammonia or alkylamine is reacted under boiling conditions with an alkane- or arenesulfonyl halide in the absence of an added solvent. The heat of reaction is dissipated by the heat of vaporization of the ammonia or alkylamine.

10 Claims, No Drawings

PROCESS FOR THE PREPARATION OF ALKANE- AND ARENESULFONAMIDES

BACKGROUND OF THE INVENTION

The invention relates to alkane- and arenesulfonamides, and more particularly to a novel process for their preparation.

Synthetic methods for organosulfonamides in general, and for alkanesulfonamides in particular, are well known in the literature. Many of these methods involve treating the corresponding sulfonyl chloride with ammonia or a primary or secondary amine in the presence of an organic solvent. Such processes yield an initially crude product which is contaminated with by-products. The crude product requires purification before it may be used further.

European Patent Application 0276182 describes the preparation of $C_1$–$C_4$ alkanesulfonamides using di- or monoalkoxyalkane solvents.

U.S. Pat. No. 3,300,529 describes a process for preparing N-alkyl and N,N-dialkyl-substituted ethylenesulfonamides by simultaneous dehydrochlorination and amination of $\beta$-chloro-alkanesulfonyl chlorides in any reactive solvent.

U.S. Pat. No. 3,781,441 describes a process for making 4-chloro-3,5-dinitrobenzenesulfonamide from the corresponding sulfonyl chloride by reaction with ammonia in various solvents at temperatures below 10° C. Here the process of the patent is concerned with avoiding displacement of the aryl chlorine by ammonia.

U.S. Pat. No. 3,574,740 describes the preparation of methanesulfonamide and its derivatives by treating methanesulfonyl chloride in $C_1$ to $C_4$ nitroalkane with ammonia or a primary or secondary amine. Substitution of other solvents is not suggested. As stated in this patent, the solubility of methanesulfonamide in nitroalkanes is highly temperature dependent, requiring filtration at elevated temperature to remove by-products. Processing in nitroalkanes produces discolored products. Further processing is required in the nature of hot filtrations and removal of undesired color from the product.

Czechoslovakia Patent 235,626 describes treatment of methanesulfonyl chloride in solution in toluene with gaseous ammonia followed by crystallization of the methanesulfonamide product from a toluene/ethanol mixture after concentration. Ammonium chloride is soluble in the toluene/ethanol reaction mixture to over 1% by weight concentration. The product must be isolated by crystallization from the concentrated reaction mixture to separate it from the ammonium chloride remaining in solution. This results in a drop in yield to about 90%. On a large scale, this small drop in yield can have significant economic consequences.

Treatment of methanesulfonyl chloride in benzene with anhydrous ammonia to give the desired methanesulfonamide is described in the following: Field et al., J. Am. Chem. Soc., Vol. 75, pages 934–937 (1953); Field et al., J. Am. Chem. Soc., Vol. 77, pages 170–171 (1955); Pantlitschko et al., Monatsh., Vol. 89, pages 285–87 (1958), as summarized in Chem Abstracts 53:1140i (1959); and Dutt, J. Chem. Soc., Vol. 125, pages 1463–65 (1924).

Zhur. Obschei Khim., Vol 18, pages 729–32 (1948), as summarized in Chem. Abstracts 43:120f, describes treatment of methanesulfonyl chloride in dry diethyl ether with anhydrous ammonia, followed by evaporation of solvent and extraction of the residue with benzene to obtain the methanesulfonamide product.

Benzene is a known carcinogen and, while it can be handled industrially, its use complicates any process in which it is employed.

The preparation of N-substituted alkanesulfonamides from alkanesulfonyl chlorides and amines is reported by Sacco et al., J. Am. Chem. Soc., 76, 303–305 (1985).

Chem. Abstracts 56:7116f, abstracting Sokolsku et al., Izvest. Akad Nauk S.S.S.R., Otdel Khem Nauk 1606 (1968), describes the reaction of $CH_3SO_2F$ with $(C_2H_5)_2NH$ after one day to give 96.5% $CH_3SO_2N(C_2H_5)_2$.

Liquid ammonia is reacted with 1,2,4-triazol-3-sulfonylchloride to give 1,2,4-triazol-3-sulfonamide in U.S. Pat. No. 2,554,816.

The reaction of alkane- and arenesulfonyl halides with ammonia or amines is extremely exothermic. The rate at which these reactants may be contacted is therefore limited by the rate at which the heat of reaction may be removed. The release of the heat of reaction has been controlled according to the prior art, by slow addition of the reactants, resulting in a concomitantly slower production rate.

What is needed is a method for the rapid, direct synthesis of alkane- or arenesulfonamides which produces minimal by-products, and which dispenses with large volumes of solvent in the primary reaction phase.

SUMMARY OF THE INVENTION

The invention provides a process for the preparation of alkane- and arenesulfonamides having the formula:

$$RSO_2NR^1R^2$$

wherein

R is selected from $C_1$ to $C_{20}$ alkyl, $C_6$ to $C_{20}$ aryl, substituted $C_1$ to $C_{20}$ alkyl and substituted $C_6$ to $C_{20}$ aryl; and $R_1$ and $R_2$, which may be the same or different, are selected from hydrogen, $C_1$ to $C_{20}$ alkyl, and $C_6$ to $C_{20}$ aryl, which process comprises treating an alkane- or arenesulfonyl halide having the formula:

$$RSO_2X$$

wherein R is as defined above and X is fluorine, chlorine, bromine or iodine, with a compound of the formula:

$$HNR^1R^2$$

at boiling conditions wherein $R^1$ and $R^2$ are as defined above, in the absence of an additional solvent. The reaction is carried out at a pressure which maintains the reaction temperature in the range from about $-20°$ C. to about 150° C.

As used in the herein specification and appended claims, "boiling conditions" means any combination of temperature and pressure at which a reactant or reactants is at boil.

DETAILED DESCRIPTION OF THE INVENTION

We have found that the rapid reaction of alkane- or arenesulfonyl halides with excess ammonia or amines to form the corresponding alkane- or arenesulfonamide is possible in the absence of added solvents by maintaining the reaction mixture at boiling conditions, at a pressure, either positive, negative, or atmospheric, which maintains the reaction temperature in the range of from about −20° C. to about 150° C. By "positive pressure" is meant a pressure greater than one atmosphere. By "negative pressure" is meant a pressure less than one atmosphere.

The large excess of boiling ammonia or amine reactant acts as a heat-sink, controlling the evolution of heat due to reaction, and allowing the reactants to be contacted at substantially more rapid rates than previously utilized. This in turn permits higher production rates without the use of costly refrigeration. The invention utilizes the heat of vaporization of the ammonia or amine to dissipate the exceptionally high heat of reaction of the process.

For ammonia, which has a boiling point of about −31° C. at one atmosphere, and for low boiling amines, that is, amines which boil at a temperature below about 150° C. at one atmosphere, the reaction is carried out under positive pressure to contain the volatile ammonia/amine in the reaction system under refluxing conditions. When the amine reactant comprises a higher boiling amine, that is, an amine with a boiling point above about 150° C. at one atmosphere, it may be necessary to conduct the reaction under negative pressure, i.e., vacuum, in order to induce boiling of the amine at a reaction temperature below 150° C.

Reaction temperatures above about 150° C. are not desirable since degradation of the reactants or product may occur, leading to the production of unwanted by-products. Reaction temperatures below about −20° C. are not practical since the rate of reaction is too slow.

According to the process of the invention, alkane-or arenesulfonamides may be prepared in batch, semi-continuous or continuous fashion.

In one embodiment of the invention, an alkane- or arenesulfonyl halide, such as for example methanesulfonyl chloride, is contacted with an effective amount of $HNR^1R^2$, for example ammonia, at superatmospheric pressure, at room temperature or above. The reaction is normally rapid and is usually complete by the time the addition of reagents to the contact or treatment zone is completed.

The exothermic heat of reaction may be readily removed, and the reaction temperature controlled precisely, by carrying out the reaction under boiling conditions. The $HNR^1R^2$ is brought to boil by the heat of reaction generated by the reaction of $HNR^1R^2$ and $RSO_2X$. The heat of reaction is removed by condensing the boiled-up vapors of $HNR^1R^2$, and returning the condensate to the reaction liquid. According to one preferred embodiment of the invention, the reaction is carried out under pressurized boiling conditions to produce a boiled-up vapor which is substantially pure $HNR^1R^2$.

Preferably, any excess $HNR^1R^2$ remaining in the reaction mixture at the conclusion of the reaction is removed, such as by venting. When the process is conducted in batch fashion, the reaction is deemed concluded when substantially no unreacted $RSO_2X$ remains in the reaction mixture.

Where the $HNR^1R^2$ compound is ammonia, ammonium halide is produced as a by-product. Where the $HNR^1R^2$ compound is an amine, the by-product of the reaction is an amine hydrohalide. The by-product remains in the reaction mixture with the desired arenesulfonamide or alkanesulfonamide product following removal of excess $HNR^1R^2$. The amine hydrohalide may be separated from the sulfonamide product by any convenient method known to those skilled in the art for separating such materials. For example, the amine hydrohalide may be treated with an alkali metal hydroxide, e.g. sodium or potassium hydroxide, to form the corresponding alkali halide salt, for example, sodium chloride or potassium chloride. Formation of the salt results in the generation of free ammonia or alkylamine, which may be recovered. The alkane- or arenesulfonamide is stable under these reaction conditions.

The resulting mixture of the desired alkane- or arenesulfonamide product and alkali halide salt may be directly utilized in those sulfonamide applications wherein salt may be tolerated. Alternatively, the desired sulfonamide product may be recovered from the salt by conventional means such as solvent extraction with filtration and concentration of the filtrate. Solvents for this purpose include, for example, alcohols, ethers, cyclic ethers, tetrahydrofuran, mono- or dialkoxyethane, and the like.

The $C_1$, $C_2$, $C_3$, $C_4$ and $C_8$ alkanesulfonyl halide starting materials are all commercially available. The other starting materials contemplated in the practice of the invention may be prepared by synthetic methods well known to those skilled in the art. For example, U.S. Pat. No. 3,626,004, the entire disclosure of which is incorporated herein by reference, teaches a general method for preparation of alkanesulfonyl chlorides from the corresponding alkyl mercaptan or dialkyl disulfide. Alkane- or arenesulfonyl chlorides are particularly preferred starting materials in the practice of the invention.

Specific $C_1$ to $C_{20}$ alkyl and $C_6$ to $C_{20}$ aryl moieties preferred for the starting materials in the process of the invention include, without limiting the generality of the foregoing, methyl, ethyl, i-propyl, t-butyl, n-butyl, n-octyl, decyl, dodecyl, cyclohexyl, cyclopentyl, phenyl, naphthyl, tolyl, xylyl, benzyl, and the like. $C_1$ to $C_4$ alkanesulfonyl chlorides are particularly preferred as $RSO_2X$ compounds. Ammonia and diethylamine are preferred as $HNR^1R^2$ compounds. The reaction of methylsulfonyl halides and diethylamine yields N,N-diethylmethanesulfonamide.

The $C_1$–$C_{20}$ alkyl or $C_6$–$C_{20}$ aryl moiety R of the $RSO_2X$ reactant, and the corresponding moiety of the $RSO_2NR^1R^2$ product, is optionally substituted. The optional substition may comprise any substituent or combination of substituents which will not interfere with the reaction between the $RSO_2X$ halide and the $HNR^1R^2$ amine, under the reaction conditions described herein. The substituent or substituents should not be of such a nature that side reactions among the $RSO_2X$ molecules, or between the $RSO_2X$ and $HNR^1R^2$ reactants, can occur. Such side reactions involving substituents of the $C_1$–$C_{20}$ alkyl or $C_6$–$C_{20}$ aryl moiety can lead to the formation of unwanted side products. In particular, the optional substituents should be selected such that they will not be reactive under the reaction conditions, since the environment of the reaction between the halide and ammonia or amine reactants is substantially basic due to the excess ammonia or amine that is present.

Typical of substituents which may satisfactorily form a portion of the $C_1$–$C_{20}$ alkyl and $C_6$–$C_{20}$ aryl moieties, R, comprise aryl and $C_1$–$C_{20}$ alkyl or arylalkyl. Other possible substituents which will not interfere with the reaction between $RSO_2X$ and $HNR^1R^2$ under the conditions described herein will be readily apparent to those skilled in the art.

The order of addition of reactants is not particularly critical for most reaction conditions, but it is preferred to add the alkanesulfonyl halide or arenesulfonyl halide to an excess of $HNR^1R^2$ to obtain the highest purity product.

The reaction may be conveniently conducted at a rate at which the available cooling capacity will be adequate to maintain the desired reaction conditions, e.g., temperature and pressure. The reaction or treatment time is not critical. Normally, the reaction will be complete after complete addition of all reactants in a batch reaction. In a continuous or semi-continuous reaction, one may control the relative feed rate of the reactants into the reactant contact zone, and control the rate of flow of the reaction mixture, through and out of the contact zone, so that the reaction is essentially complete. Control of reactant feed rates and flow rates through the contact zone may be achieved by employing standard monitoring techniques well known to those skilled in the art.

Although the process of the invention has been specifically illustrated herein by reference to alkanesulfonyl chlorides, it is readily recognized that other alkanesulfonyl halides, or arenesulfonyl halides, such as alkane- or arenesulfonyl fluorides, bromide and iodides, may be substituted for the specifically illustrated chlorides.

Although the process of the invention has been illustrated in the hereinafter examples by the use of a reaction performed from about room temperature (about 20°-25° C.) to about 50° C., the temperature of the reaction can vary over the range of from about −20° C. to about 150° C. Preferably it may range from about 10° C. to about 70° C.

The reaction temperature is maintained at a temperature in the range of from about −20° C. to about 150° C. by selecting the appropriate pressure. Regulation of the pressure, and hence the reaction temperature, may be achieved by methods well known to those skilled in the art. It will be readily appreciated that for ammonia and the lowest boiling amines, e.g., dimethylamine (b.p. = 7° C.), the reaction is advantageously conducted under positive pressure, such as a suitable autoclave apparatus. Similarly, when the $HNR^1R^2$ reactant comprises a higher boiling amine, i.e., an amine which boils above 150° C. at atmospheric pressure, the reaction should be conducted under a negative pressure sufficient to depress the boiling point of the amine to 150° C. or below.

An effective amount of $HNR^1R^2$ to be employed in the reaction will be at least the two molar stoichiometric equivalent amount, and will preferably be an excess over that amount sufficient to provide a free flowing fluid reaction medium. Excess $HNR^1R^2$ may, of course, be recovered from the final reaction mixture by know conventional means. For example, when ammonia is the $HNR^1R^2$ compound, excess ammonia may be recovered by venting the pressure from the reaction mixture and compression and/or condensation back to a liquid.

The following non-limiting examples further illustrate the process of their invention.

EXAMPLE 1

Preparation Of Methanesulfonamide Using Liquid Ammonia

A stirred, 1-liter, dry, stainless steel autoclave equipped with a 2ft-stainless steel condenser and addition inlets for ammonia, methanesulfonyl chloride (MSC), water and nitrogen gas was evacuated using a vacuum pump and then charged with 320 grams (18.8 moles) of ammonia. The autoclave was warmed to about 33° C., while the pressure was maintained by a pressure control valve set at 150 psig. The ammonia was refluxed at this pressure. Then the MSC (2.32 g, 2.02 moles) was added over a period of 10 minutes by means of nitrogen pressure while the temperature of the reactor increased to 51° C. The MSC addition was determined to be complete when the vapor temperature at the top of the condenser started to drop and the pressure in the reactor increased to equal the nitrogen pressure used to feed the MSC. At this point the MSC line was shut off. A quantitative recovery of the crude product ($CH_3SO_2NH_2 + NH_4Cl$) was obtained. NMR (in $d_6$-DMSO) analysis (TMS standard) indicated that additionally there was produced 1.7 mole % ammonium methanesulfonamide and 0.95 mole %, ammonium salt of methanesulfonic acid, based on the methanesulfonamide content. The detailed results are:

| $H^1$ NMR (TMS Standard Coupling): | | |
|---|---|---|
| $H^1$ Chemical Shift (ppm) | Coupling (Hz) | Assignments |
| 7.49 | Broad | $NH_4^+$ |
| 6.92 | Broad | $NH_2$ of $CH_3SO_2NH_2$ |
| 3.00 | Singlet | $CH_3$ of $CH_3SO_2NH_2$ |
| 2.81 | Singlet | $CH_3$ of $(CH_3SO_2)_2NH$ |
| 2.55 | Singlet | $CH_3$ of $CH_3SO_3-NH_4^+$ |

COMPARATIVE EXAMPLE 2

Preparation Of Methanesulfonamide Using Aqueous Ammonium Hydroxide

To a 500 ml. 3-necked glass flask equipped with a condenser, thermocouple, an inlet for addition of MSC via a syringe pump (⅛ inch Teflon ® tubing) was charged 232.0 g (4.0 moles, 29%) of ammonium hydroxide at 25° C. Then MSC (115 g, 1.0 mole) was added over 1 hr. at a temperature of 11 to 23° C. Then an aliquot of the reaction mixture was taken, and water stripped off under reduced pressure at 60° C. to obtain a quantitative yield of solids (methanesulfonamide and ammonium chloride). The NMR proton analysis in $d_6$-DMSO (TMS Standard) indicated 6.4 mole % of the ammonium salt of methanesulfonic acid and 1.7 mole % of the ammonium salt of methane sulfonamide.

| $H^1$ Chemical Shift (ppm) | Coupling (Hz) | Assignments |
|---|---|---|
| 7.51 | Singlet | $NH_4^+$ |
| 6.92 | Singlet | $NH_2$ of $CH_3SO_2NH_2$ |
| 2.97 | Singlet | $CH_3$ of $CH_3SO_2NH_2$ |
| 2.81 | Singlet | $CH_3$ of $(CH_3SO_2)_2NH$ |
| 2.55 | Singlet | $CH_3$ of $CH_3SO_3-NH_4^+$ |

A comparison of the data for Example 2 with that of Example 1 indicates that the use of aqueous ammonium hydroxide in place of boiling liquid ammonia gives significantly more hydrolysis of the methanesulfonyl chloride to sulfonate salt.

EXAMPLE 3

Fed-batch Reactor

A pressurized stirred-tank reactor is charged with liquid $NH_3$. The reactor is equipped with a vent condenser to return condensed $NH_3$ vapors to the reactor. Alkanesulfonyl chloride is charged to the reactor over a period of time. Upon contacting the $NH_3$, the alkanesulfonyl chloride is converted to the corresponding sulfonamide and $NH_4Cl$, releasing heat. The heat release causes the unreacted ammonia to boil, which is in turn condensed and returned to the reactor. The rate of alkanesulfonyl chloride addition is limited only by the maximum rate at which the vent condenser can remove heat. The total charge of alkanesulfonyl chloride is less than the stoichiometric amount, relative to the initial $NH_3$ charge, thereby assuring that all of the alkanesulfonyl chloride is consumed. After the alkanesulfonyl chloride addition is complete, the reaction mixture containing sulfonamide, $NH_4Cl$, and excess $NH_3$, is processed to recover the sulfonamide.

EXAMPLE 4

Continuous - Stirred Tank Reactor

A pressurized stirred-tank reactor is fitted with a vent condenser. Liquid $NH_3$ and alkanesulfonyl chloride are fed continuously to the reactor under pressure, where the alkanesulfonyl chloride is converted to sulfonamide and $NH_4Cl$, releasing heat. The $NH_3$:alkanesulfonyl chloride feed ratio is greater than stoichiometric, assuring that all of the alkanesulfonyl chloride is consumed. The heat release causes the excess $NH_3$ to boil, which is condensed and returned to the reactor. The residence time in the reactor may be as short as a few seconds or minutes, approaching the intrinsic (kinetically limited) reaction rate, provided that the vent condenser is sufficiently sized to absorb the rate of heat evolution. The reactor effluent, containing sulfonamide, $NH_4Cl$ and the excess $NH_3$, is processed to recover the sulfonamide.

EXAMPLE 5

Continuous Vertical Gradient Reactor

A vertical pipe, preferably fitted with "static mixing" elements in the lower section, with a draw-off point intermediate in height along the pipe, is connected to a heat exchanger via the upper outlet of the pipe. $NH_3$ and alkanesulfonyl chloride are fed continuously under pressure to the bottom inlet of the pipe reactor, where they mix, and the alkanesulfonyl chloride converts to sulfonamide, releasing heat. The $NH_3$:alkanesulfonyl chloride feed ratio at the reactor inlet is in excess of the stoichiometric amount. Sufficient excess $NH_3$ is present at the reactor to ensure that the heat of reaction is insufficient to evaporate all of the excess $NH_3$. In this manner sufficient $NH_3$ excess is present at the entrance to the reactor so that all of the heat release from the reaction is absorbed by vaporizing $NH_3$, with some excess $NH_3$ remaining in the liquid. The boiling $NH_3$ causes the reaction mixture to become more depleted in $NH_3$ as it rises through the reaction pipe. The reactor effluent exits via the intermediate draw-off point, while the evaporated $NH_3$ exits via the top outlet of the reaction pipe. The $NH_3$ vapors are condensed by a heat exchanger, and recycled to the $NH_3$ inlet to the reactor.

The reactor effluent from Examples 1, 3, 4 or 5, containing alkanesulfonamide, $NH_4Cl$, and non-evaporated excess $NH_3$, may be processed to recover the alkanesulfonamide as described in Example 6 or 7.

EXAMPLE 6

Recovery Of High Purity Sulfonamide With $NH_4Cl$ As By-product

The reactor effluent from Examples 1, 3, 4 or 5 is depressurized, allowing the excess $NH_3$ to flash-off. The $NH_3$ is recovered for recycle (e.g., by cold condensation or compression), or is absorbed by a scrubber. The depressurization causes the $NH_4Cl$ and sulfonamide to precipitate out. The depressurized effluent, containing the sulfonamide and $NH_4Cl$, is heated above the melting point of the sulfonamide, producing a slurry of molten sulfonamide and precipitated $NH_4Cl$. The alkanesulfonamide is separated from the precipitate -.by conventional means, e.g., solid/liquid separations, such as filtration or centrifugation; distillation under high vacuum; and solvent extraction.

EXAMPLE 7

Recovery Of Sulfonamide Containing Salt. With No $NH_4Cl$ By-product

The reactor effluent from Examples 1, 3, 4 or 5 is mixed with an aqueous alkali metal hydroxide, e.g., caustic. The $NH_4Cl$ reacts with the alkali metal hydroxide, forming the alkali metal chloride, water and $NH_3$. The caustic-treated mixture is depressurized allowing the excess and generated $NH_3$ to flash off. The depressurized mixture is an aqueous solution of alkanesulfonamide and salt. The water is boiled off, and the residue is heated above the melting point of sulfonamide. The salt precipitates out from the melt, forming a slurry. The molten sulfonamide/salt slurry is taken as the product (salt may be tolerated as an inert in certain applications of sulfonamide). Alternatively, the sulfonamide is separated from the precipitated salt by conventional means, e.g., solid/liquid separations such as filtration or centrifugation; distillation under high vacuum; a solvent extraction.

The products of the invention are liquids, crystalline or waxy solids. They find utility as synthetic intermediates in the manufacture of agricultural chemicals, chemicals useful in the treatment of textiles and paper, and as solvents. Halogenated derivatives are particularly valuable in flameproofing and waterproofing.

The present invention may be embodied in other specific forms without departing from the spirit or essential attributes thereof and, accordingly, reference should be made to the appended claims, rather than to the foregoing specification, as indicating the scope of the invention.

We claim:

1. A process for the preparation of alkane- and arenesulfonamides having the formula $RSO_2NH_2$, wherein R is selected from $C_1$ to $C_{20}$ alkyl, $C_6$ to $C_{20}$ aryl, substituted $C_1$ to $C_{20}$ alkyl, and substituted $C_6$ to $C_{20}$ aryl, wherein the substituent groups are inert to the reaction, which proces comprises treating with ammonia, in the absence of an additional solvent, an alkane- or arenesulfonyl halide having the formula:

$$RSO_2X$$

wherein R is as defined above and X is fluorine, chlorine, bromine or iodine, the reaction being carried out at a selected pressure which controls the reaction at a pre-selected temperature in the range of from about −20° C. to about 132° C., said ammonia being brought to boil by the heat of reaction generated by its reaction with $RSO_2X$, and said heat of reaction being removed by condensing the boiled-up ammonia vapors and returning the condensate to the reaction liquid.

2. A process according to claim 1 wherein following completion of the reaction, excess ammonia is removed from the reaction mixture.

3. A process according to claim 1 wherein the reaction is carried out under pressurized boiling conditions to produce a boiled-up vapor which is substantially pure ammonia.

4. A process according to claim 1 wherein $RSO_2X$ is a $C_1$ to $C_4$ alkanesulfonyl chloride.

5. A process according to claim 4 wherein $RSO_2X$ is methanesulfonyl chloride.

6. A process according to claim 1 wherein the reaction temperature is in the range of from about 10° C. to about 70° C.

7. A process according to claim 1 which is run as a batch process.

8. A process according to claim 1 which is run as a semi-continuous process.

9. A process according to claim 1 which is run as a continuous process.

10. A process according to claim 1 comprising the additional step of separating an amine hydrohalide by product from the alkane- or arenesulfonamide product.

* * * * *